(12) United States Patent
Murphy

(10) Patent No.: US 8,585,660 B2
(45) Date of Patent: Nov. 19, 2013

(54) VALVED CATHETER WITH POWER INJECTION BYPASS

(75) Inventor: Nathan Murphy, South Boston, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 1285 days.

(21) Appl. No.: 11/339,217

(22) Filed: Jan. 25, 2006

(65) Prior Publication Data

US 2007/0173777 A1   Jul. 26, 2007

(51) Int. Cl.
*A61M 5/00* (2006.01)

(52) U.S. Cl.
USPC .......................................... 604/247; 604/248

(58) Field of Classification Search
USPC ................................... 604/246–248
See application file for complete search history.

(56) References Cited

U.S. PATENT DOCUMENTS

| | | |
|---|---|---|
| 2,446,571 A | 3/1944 | Browne |
| 2,720,881 A | 10/1955 | Weaver et al. |
| 2,755,060 A | 7/1956 | Twyman |
| 3,113,586 A | 12/1963 | Edmark, Jr. |
| 3,159,175 A | 12/1964 | MacMillan |
| 3,159,176 A | 12/1964 | Russell et al. |
| 3,477,438 A | 11/1969 | Allen et al. |
| 3,514,438 A | 5/1970 | Nelsen et al. |
| 3,525,357 A | 8/1970 | Koreski |
| 3,621,557 A | 11/1971 | Cushman et al. |
| 3,669,323 A | 6/1972 | Harker et al. |
| 3,673,612 A | 7/1972 | Merrill et al. |
| 3,674,183 A | 7/1972 | Venable et al. |
| 3,710,942 A | 1/1973 | Rosenberg |
| 3,788,327 A | 1/1974 | Donowitz et al. |
| 3,811,466 A | 5/1974 | Ohringer |
| 3,955,594 A | 5/1976 | Snow |
| 4,072,146 A | 2/1978 | Howes |
| 4,142,525 A | 3/1979 | Binard et al. |
| 4,143,853 A | 3/1979 | Abramson |
| 4,244,379 A | 1/1981 | Smith |
| 4,387,879 A | 6/1983 | Tauschinski |
| 4,405,316 A | 9/1983 | Mittleman |

(Continued)

FOREIGN PATENT DOCUMENTS

| | | |
|---|---|---|
| DE | 20208420 | 10/2002 |
| EP | 0128625 | 12/1984 |

(Continued)

OTHER PUBLICATIONS

Asch, "Venous access: options, approaches and issues," Can Assoc. Radiol J., vol. 52, No. 3 pp. 153-164 (2001).

(Continued)

*Primary Examiner* — Kevin C Sirmons
*Assistant Examiner* — Deanna K Hall
(74) *Attorney, Agent, or Firm* — Ryan D. Artis

(57) ABSTRACT

A valve assembly for a catheter comprising a housing having a lumen extending therethrough a first port opening to a proximal end of the lumen via a first port passage and a valve disposed in the first port passage, the valve being biased toward a closed configuration to prevent fluid flow therethrough when the first port passage is not in use in combination with a second port opening of the housing in fluid connection with a proximal end of the lumen via a second port passage.

7 Claims, 2 Drawing Sheets

(56) References Cited

U.S. PATENT DOCUMENTS

| | | | |
|---|---|---|---|
| 4,434,810 A | 3/1984 | Atkinson |
| 4,447,237 A | 5/1984 | Frisch et al. |
| 4,468,224 A | 8/1984 | Enzmann et al. |
| 4,502,502 A | 3/1985 | Krug |
| 4,524,805 A | 6/1985 | Hoffman |
| 4,543,087 A | 9/1985 | Sommercorn et al. |
| 4,552,553 A | 11/1985 | Schulte et al. |
| 4,610,665 A | 9/1986 | Matsumoto et al. |
| 4,616,768 A | 10/1986 | Flier |
| 4,673,393 A | 6/1987 | Suzuki et al. |
| 4,681,572 A | 7/1987 | Tokarz et al. |
| 4,692,146 A | 9/1987 | Hilger |
| 4,722,725 A | 2/1988 | Sawyer et al. |
| 4,790,832 A | 12/1988 | Lopez |
| 4,798,594 A | 1/1989 | Hillstead |
| 4,801,297 A | 1/1989 | Mueller |
| 4,908,028 A | 3/1990 | Colon et al. |
| 4,944,726 A | 7/1990 | Hilal et al. |
| 4,946,448 A | 8/1990 | Richmond |
| 5,000,745 A | 3/1991 | Guest et al. |
| 5,009,391 A | 4/1991 | Steigerwald |
| 5,030,210 A | 7/1991 | Alchas et al. |
| 5,084,015 A | 1/1992 | Moriuchi |
| 5,098,405 A * | 3/1992 | Peterson et al. ............ 604/247 |
| 5,125,893 A | 6/1992 | Dryden |
| 5,147,332 A | 9/1992 | Moorehead |
| 5,149,327 A | 9/1992 | Oshiyama |
| 5,167,638 A | 12/1992 | Felix et al. |
| 5,169,393 A | 12/1992 | Moorehead et al. |
| 5,176,652 A | 1/1993 | Littrell |
| 5,176,662 A | 1/1993 | Bartholomew et al. |
| 5,201,722 A | 4/1993 | Moorehead et al. |
| 5,205,834 A | 4/1993 | Moorehead et al. |
| 5,249,598 A | 10/1993 | Schmidt |
| 5,254,086 A | 10/1993 | Palmer et al. |
| 5,324,274 A | 6/1994 | Martin |
| 5,330,424 A | 7/1994 | Palmer et al. |
| 5,336,203 A | 8/1994 | Goldhardt et al. |
| 5,360,407 A | 11/1994 | Leonard et al. |
| 5,370,624 A | 12/1994 | Edwards et al. |
| 5,395,352 A | 3/1995 | Penny |
| 5,396,925 A | 3/1995 | Poli et al. |
| 5,399,168 A | 3/1995 | Wadsworth et al. |
| 5,401,255 A | 3/1995 | Sutherland et al. |
| D357,735 S | 4/1995 | McPhee |
| 5,405,340 A | 4/1995 | Fageol et al. |
| 5,411,491 A | 5/1995 | Goldhardt et al. |
| 5,453,097 A | 9/1995 | Paradis |
| 5,454,784 A | 10/1995 | Atkinson et al. |
| 5,469,805 A | 11/1995 | Gibbs et al. |
| 5,470,305 A | 11/1995 | Arnett et al. |
| 5,484,420 A | 1/1996 | Russo |
| 5,542,923 A | 8/1996 | Ensminger et al. |
| 5,554,136 A | 9/1996 | Luther |
| 5,562,618 A | 10/1996 | Cai et al. |
| 5,571,093 A | 11/1996 | Cruz et al. |
| 5,575,769 A | 11/1996 | Vaillancourt et al. |
| 5,624,395 A | 4/1997 | Mikhail et al. |
| 5,637,099 A | 6/1997 | Durdin et al. |
| 5,667,500 A | 9/1997 | Palmer et al. |
| 5,707,357 A | 1/1998 | Mikhail et al. |
| 5,743,873 A | 4/1998 | Cai et al. |
| 5,743,884 A | 4/1998 | Hasson et al. |
| 5,743,894 A | 4/1998 | Swisher |
| 5,752,938 A | 5/1998 | Flatland et al. |
| 5,803,078 A | 9/1998 | Brauner |
| 5,807,349 A | 9/1998 | Person et al. |
| 5,810,789 A | 9/1998 | Powers et al. |
| 5,843,044 A | 12/1998 | Moorehead |
| 5,853,397 A | 12/1998 | Shemesh et al. |
| 5,865,308 A | 2/1999 | Qin et al. |
| 5,944,698 A | 8/1999 | Fischer et al. |
| 5,984,902 A | 11/1999 | Moorehead |
| 6,033,393 A | 3/2000 | Balbierz et al. |
| 6,045,734 A | 4/2000 | Luther et al. |
| 6,050,934 A | 4/2000 | Mikhail et al. |
| 6,056,717 A | 5/2000 | Finch et al. |
| 6,062,244 A | 5/2000 | Arkans |
| 6,092,551 A | 7/2000 | Bennett |
| 6,099,505 A | 8/2000 | Ryan et al. |
| 6,120,483 A | 9/2000 | Davey et al. |
| 6,152,909 A | 11/2000 | Bagaoisan et al. |
| 6,210,366 B1 | 4/2001 | Sanfilippo |
| 6,227,200 B1 | 5/2001 | Crump et al. |
| 6,270,489 B1 | 8/2001 | Wise et al. |
| 6,306,124 B1 | 10/2001 | Jones et al. |
| 6,364,861 B1 | 4/2002 | Feith et al. |
| 6,364,867 B2 | 4/2002 | Wise et al. |
| 6,375,637 B1 | 4/2002 | Campbell et al. |
| 6,436,077 B1 | 8/2002 | Davey et al. |
| 6,442,415 B1 | 8/2002 | Bis et al. |
| 6,446,671 B2 | 9/2002 | Armenia et al. |
| 6,508,791 B1 | 1/2003 | Guerrero |
| 6,551,270 B1 | 4/2003 | Bimbo et al. |
| 6,610,031 B1 | 8/2003 | Chin |
| 6,726,063 B2 | 4/2004 | Stull et al. |
| 6,786,884 B1 | 9/2004 | DeCant et al. |
| 6,874,999 B2 | 4/2005 | Dai et al. |
| 6,953,450 B2 * | 10/2005 | Baldwin et al. ............... 604/248 |
| 6,994,314 B2 | 2/2006 | Garnier et al. |
| 7,081,106 B1 | 7/2006 | Guo et al. |
| 7,252,652 B2 | 8/2007 | Moorehead et al. |
| 7,291,133 B1 | 11/2007 | Kindler et al. |
| 7,316,655 B2 | 1/2008 | Garibotto et al. |
| 7,435,236 B2 | 10/2008 | Weaver et al. |
| 7,601,141 B2 | 10/2009 | Dikeman et al. |
| 7,637,893 B2 | 12/2009 | Christensen et al. |
| 7,758,541 B2 | 7/2010 | Wallace et al. |
| 2001/0023333 A1 | 9/2001 | Wisse et al. |
| 2001/0037079 A1 | 11/2001 | Burbank et al. |
| 2002/0010425 A1 | 1/2002 | Guo et al. |
| 2002/0016584 A1 | 2/2002 | Wise et al. |
| 2002/0121530 A1 | 9/2002 | Socier |
| 2002/0156430 A1 | 10/2002 | Haarala et al. |
| 2002/0165492 A1 | 11/2002 | Davey et al. |
| 2002/0193752 A1 | 12/2002 | Lynn |
| 2003/0122095 A1 | 7/2003 | Wilson et al. |
| 2004/0034324 A1 | 2/2004 | Seese et al. |
| 2004/0064128 A1 | 4/2004 | Raijman et al. |
| 2004/0102738 A1 | 5/2004 | Dikeman |
| 2004/0108479 A1 | 6/2004 | Garnier et al. |
| 2004/0186444 A1 | 9/2004 | Daly et al. |
| 2004/0193119 A1 | 9/2004 | Canaud et al. |
| 2004/0210194 A1 | 10/2004 | Bonnette et al. |
| 2004/0267185 A1 | 12/2004 | Weaver et al. |
| 2005/0010176 A1 | 1/2005 | Dikeman et al. |
| 2005/0027261 A1 | 2/2005 | Weaver et al. |
| 2005/0043703 A1 | 2/2005 | Nordgren |
| 2005/0049555 A1 | 3/2005 | Moorehead et al. |
| 2005/0149116 A1 | 7/2005 | Edwards et al. |
| 2005/0171490 A1 | 8/2005 | Weaver et al. |
| 2005/0171510 A1 | 8/2005 | DiCarlo et al. |
| 2005/0283122 A1 | 12/2005 | Nordgren |
| 2006/0129092 A1 | 6/2006 | Hanlon et al. |
| 2006/0135949 A1 | 6/2006 | Rome et al. |
| 2006/0149211 A1 | 7/2006 | Simpson et al. |
| 2007/0161940 A1 | 7/2007 | Blanchard et al. |
| 2007/0161970 A1 | 7/2007 | Spohn et al. |
| 2007/0276313 A1 | 11/2007 | Moorehead et al. |
| 2008/0108956 A1 | 5/2008 | Lynn et al. |
| 2009/0292252 A1 | 11/2009 | Lareau et al. |

FOREIGN PATENT DOCUMENTS

| | | |
|---|---|---|
| EP | 0337617 | 10/1989 |
| EP | 0864336 | 9/1998 |
| EP | 0930082 | 7/1999 |
| EP | 1016431 | 7/2000 |
| FR | 2508008 | 12/1982 |
| FR | 2718969 | 10/1995 |
| GB | 966137 | 8/1964 |
| GB | 2102398 | 2/1983 |
| JP | 59133877 | 8/1984 |
| JP | 63255057 | 10/1988 |

(56) References Cited

FOREIGN PATENT DOCUMENTS

| | | |
|---|---|---|
| JP | 9038197 | 2/1997 |
| WO | WO-89/02764 | 4/1989 |
| WO | WO-91/12838 | 9/1991 |
| WO | WO-92/06732 | 4/1992 |
| WO | WO-95/16480 | 6/1995 |
| WO | WO-96/17190 | 6/1996 |
| WO | WO-96/23158 | 8/1996 |
| WO | 96 / 40359 | 12/1996 |
| WO | WO-96/41649 | 12/1996 |
| WO | WO-97/23255 | 7/1997 |
| WO | WO-97/26931 | 7/1997 |
| WO | WO-98/22178 | 5/1998 |
| WO | WO-99/42166 | 8/1999 |
| WO | WO-00/06230 | 2/2000 |
| WO | WO-00/44419 | 8/2000 |
| WO | WO-01/74434 | 10/2001 |
| WO | WO-03/084832 | 10/2003 |
| WO | WO-2005/023355 | 3/2005 |
| WO | WO-2008/089985 | 7/2008 |

OTHER PUBLICATIONS

Herts et al., "Power injection of contrast media using central venous catheters: feasibility, safety, and efficacy," AJR Am. J. Roentgenol., vol. 176, No. 2, pp. 447-453 (2001).

Roth et al., "Influence of radiographic contrast media viscosity to flow through coronary angiographic catheters," Cathet. Cardiovasc. Diagn., vol. 22, No. 4, pp. 290-294 (1991).

Carlson et al., "Safety considerations in the power injection of contrast media via central venous catheters during computered tomogrphic examinations," Invest. Radiol., vol. 27, No. 5, p. 337-340 (1992).

Kaste et al., "Safe use of powr injectors with central and peripheral venous access devices for pediatric CT," Pediatr. Radiol., vol. 26, No. 8, pp. 449-501 (1996).

Herts et al., "Power injection of intravenous contrast material through central venous catheters for CT: in vitro evaluation," Radiology, vol. 200, No. 3, pp. 731-735 (1996).

Rivitz et al., "Power injection of peripherally inserted central catheters," J. Vasc. Interv. Radiol., vol. 8, No. 5, pp. 857-863 (1997).

Rogalla et al., Safe and easy power injection of contrast material through a central line, Eur. Radiol., vol. 8, No. 1, pp. 148-149 (1998).

Williamson et al., "Assessing the adequacy of peripherally inserted central catheters for power injection of intravenous contrast agents for CT," J. Comput. Assist. Tomogr., vol. 25, No. 6, pp. 932-937 (2001).

Chahous et al., "Randomized comparison of coronary angiography using 4F catheters: 4F manual versus 'Acisted' power injection technique," Catheter Cardiovasc. Interv., vol. 53, No. 2, pp. 221-224 (2001).

Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).

Saito et al., "Diagnostic brachial coronary arteriography using a power-assisted injector and 4 French catheters with new shamps," J. Invasive Cardiol., vol. 9, No. 7, pp. 461-468 (1997).

International Search Report and Written Opinion mailed Mar. 13, 2007 for International Application No. PCT/US2006/045018 (9 pages).

International Preliminary Report on Patentability mailed Jul. 29, 2008 for International Application No. PCT/US2006/045018 (7 pages).

* cited by examiner

VALVED CATHETER WITH POWER INJECTION BYPASS

BACKGROUND OF THE INVENTION

The treatment of chronic disease often requires repeated and prolonged access to the vascular system. As it is impractical and dangerous to insert and remove a catheter at every session, patients are often fitted with a semi-permanent catheter which is left in place for months or years.

A valve may be used to seal the proximal end of such a semi-permanently implanted device when the device is not in use. One common type of valve is the Pressure Actuated Safety Valve (PASV), which open when a fluid pressure in the catheter exceeds a preselected threshold level. These PASV's often include a slitted membrane designed to remain closed when subject to pressures applied by the vascular system or through normal movement of the patient and to open when fluid pressure applied thereto to introduce fluids to or remove fluids from the vascular system.

SUMMARY OF THE INVENTION

In one aspect, the present invention is directed to a valve assembly for a catheter comprising a housing having a lumen extending therethrough a first port opening to a proximal end of the lumen via a first port passage and a valve disposed in the first port passage, the valve being biased toward a closed configuration to prevent fluid flow therethrough when the first port passage is not in use in combination with a second port opening of the housing in fluid connection with a proximal end of the lumen via a second port passage, the second port passage opening to the lumen distally of the safety valve.

DETAILED DESCRIPTION

Figure 1:
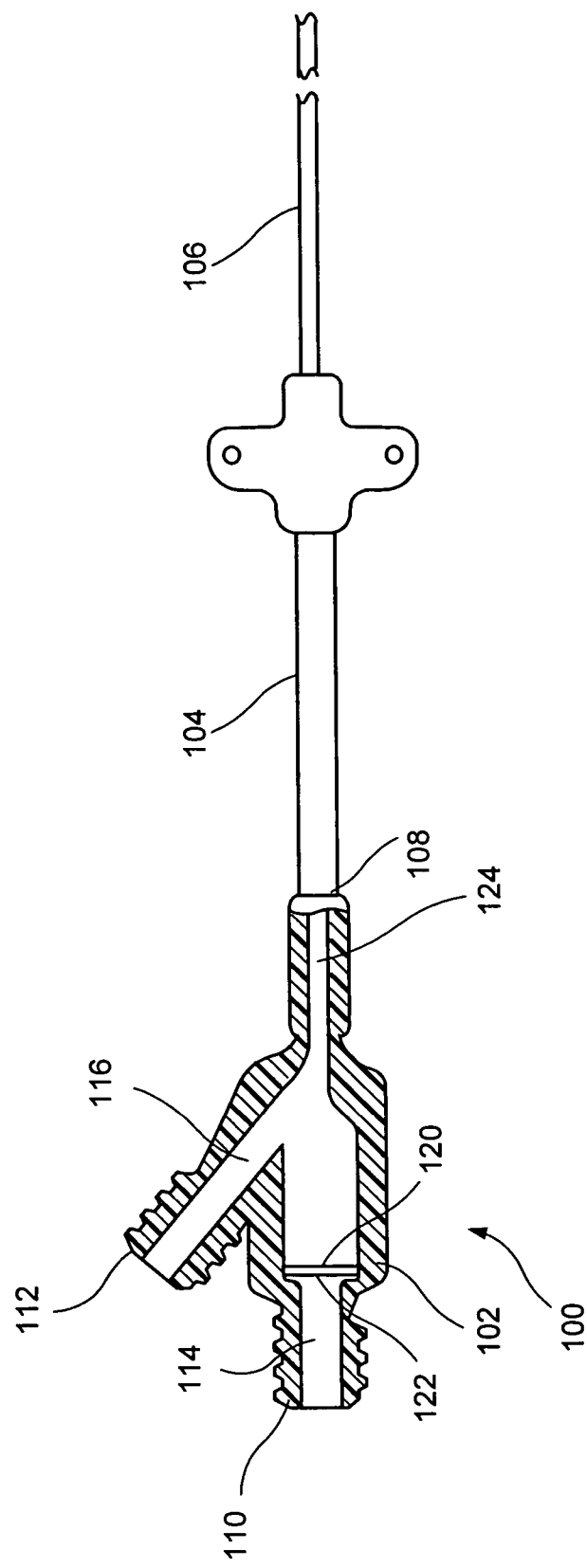
FIG. 1 is a cross sectional diagram showing an embodiment of the valve housing with a power injection bypass according to the present invention.

The present invention may be further understood with reference to the following description and the appended drawings, wherein like elements are referred to with the same reference numerals. The invention relates to devices for connecting a source of pressurized fluid to a valved catheter, without damaging the valve of the catheter. More specifically, the invention relates to a valve housing and connector for a semi-permanently implanted catheter bypassing the catheter's safety valve to avoid damage which might otherwise occur through the introduction of fluid at a high flow rate and/or pressure.

The proximal ends of semi-permanently implanted catheters generally extend out of the body and often include provisions for connection to external medical devices. For example, a semi-permanently implanted catheter may include a connector including a flow control valve which, as described above, seals the catheter when not in use and permits fluid flow therethrough when fluid transfer to and/or from the vascular system is desired. The flow control valve housing and/or the connector may be formed as a single component or may be separate from one another with either or both components coupled to the catheter or unitarily formed therewith.

Therapeutic procedures infusing fluids such as chemotherapy agents, drugs and blood products often use slower flow rates and lower injection pressures. Typically, a 10 cc syringe is the smallest that should be used and injection pressure is generally maintained less than 1 psi although pressures up to 40 psi are recommended for certain infusion pumps. However, in certain procedures fluids are administered at higher pressures and/or flow rates. For example, contrast media used in the visualization of blood vessels and structures within the body may require power injections at higher pressures and flow rates. For this reason, more robust catheters are often used for such power injection procedures—e.g., up to and over 5 cc/min.

The exemplary embodiments of the present invention allow catheters suitable for long term implantation to be used for low pressure applications as well as higher pressure applications obviating the need to insert a separate catheter for higher pressure applications. In particular, a valve housing and connector portion of a valved catheter according to the invention are designed for low pressure infusion of fluids to and withdrawal of fluids from the vascular system as well as for the power injection of fluids. The exemplary device is designed prevents damage to the safety valve that might otherwise result from a power injection through the catheter.

FIG. 1 shows an exemplary embodiment of a valve assembly 100 according to the invention. Those skilled in the art will understand that the valve assembly 100 may be permanently bonded to a catheter 104 which may, for example, be a PICC type catheter, or formed as a separate component which may be coupled thereto. The exemplary valve assembly 100 is mounted on a proximal end 108 of the catheter 104, either as a separate component or as an integral part of the catheter body 104. A distal end 106 of the catheter 104 is insertable in a conventional manner, for example to form fluid connection with the vascular system. The proximal end of the valve assembly 100 comprises an infusion port 110 through which fluids may be introduced to or removed from the body at relatively low pressures and/or flow rates. For example, as described above, the infusion of blood products chemotherapy compounds, antibiotics, drugs and other fluids provided at low pressure and flow rate can be accomplished through the infusion port 110.

The infusion port 110 of the exemplary embodiment is fluidly connected to a lumen 124 of the catheter 104 via a first passage 114 with a valve 120 controlling the flow of fluid though the first passage 114. The valve 120 prevents the leakage of fluids from the catheter 104 and the introduction of contaminants into the body via the catheter 104 and also minimizes incidences of catheter occlusion while eliminating the need for a catheter clamp or cap. For example, the valve 120 may be a pressure actuated safety valve (PASV) that comprises a slitted membrane 122 sealing the first passage 114 when the valve assembly 100 is not in use.

The slitted membrane 122 is biased to the closed configuration by, for example, tension of the elastic material from which it is manufactured. When a fluid flowing through the first passage 114 applies to the valve 120 a pressure above a predetermined threshold level, the bias of the slitted membrane 122 is overcome and the slit opens allowing fluids to pass through the valve 120. As described above, the valve 120 is preferably designed so that this threshold pressure exceeds pressures which will be applied to the valve 120 by normal anatomical activity and motions of the patient.

The valve assembly 100 also comprises a power injection port 112 designed to connect with a medical device for supplying fluid at pressures and/or flow rates exceeding levels safe for the valve 120. The power injection port 112 is in fluid communication with the lumen 124 of the catheter 104 via a second flow passage 116. In the exemplary embodiment, the second flow passage 116 and the first flow passage 114 of the infusion port 110 merge into the lumen 124 at a location downstream from the valve 120. In this manner, fluids introduced into the power injection port 112 through the flow passage 116 bypass the valve 120. Thus fluids power injected into the catheter 104 do not pass through and damage the valve 120 and the valve 120 does not limit the pressure and/or flow rates at which fluids may be injected through the valve assembly 100 and the catheter 104.

According to the exemplary embodiment shown in FIG. 1, it is not necessary to limit the pressure of the power injected fluid being injected through the catheter body 104 to prevent damage to the valve 120. This feature is especially useful when a PASV with a slitted membrane 122 is used, since the membrane 122 can easily be damaged by excessive pressure, and as a result may no longer close fully when the fluid's pressure falls below the reference pressure. According to one exemplary embodiment of the invention, the power injection fluid bypasses the portion of the catheter valve body containing the valve, so that the slitted membrane of the valve is not subjected to excessive pressures and is not damaged. Furthermore, the benefits of a valved flow path in the catheter 104 are retained simplifying the use of the catheter 104 and preventing leaks and contamination of the lumen 124.

Figure 3:
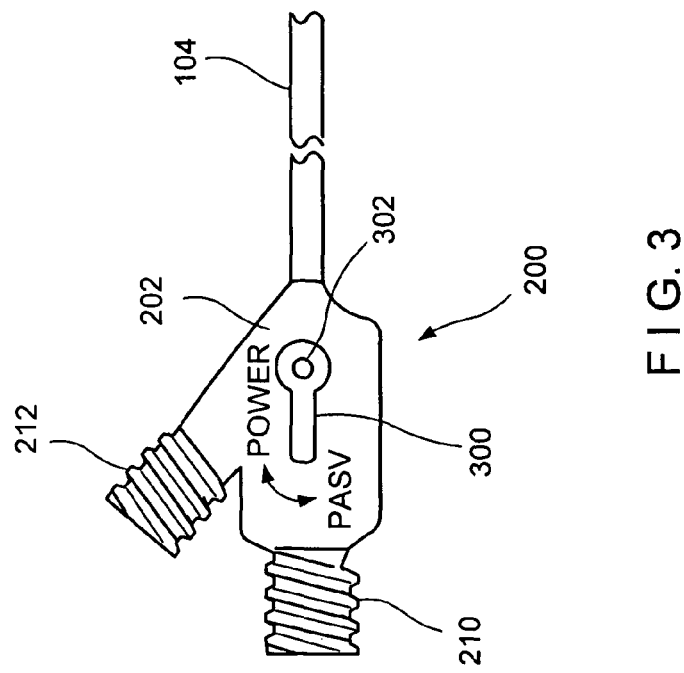
FIG. 3 is a side view of the embodiment shown in FIG. 2, having a manual lumen selector actuator.
Figure 2:
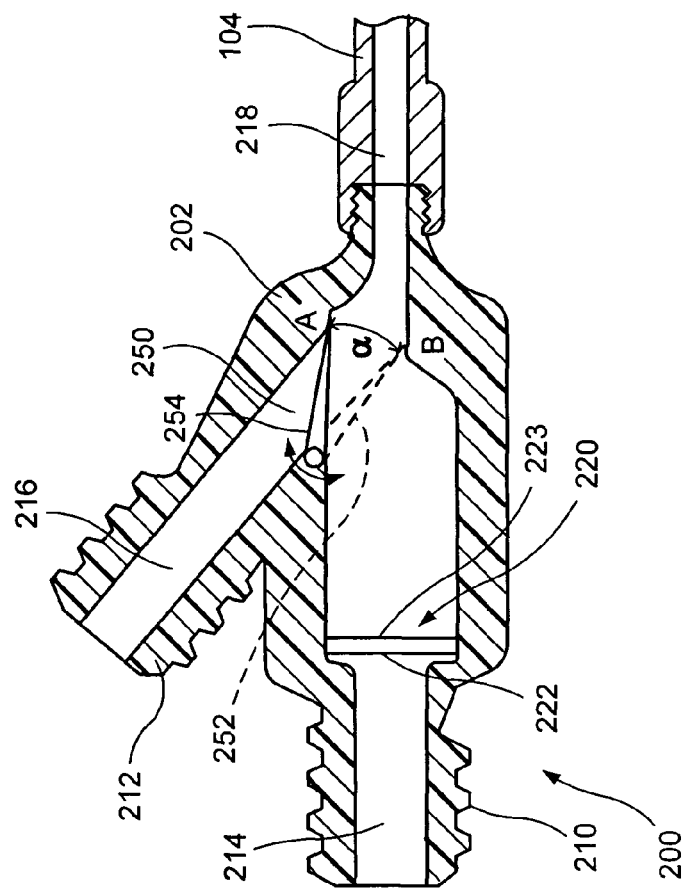
FIG. 2 is a cross sectional diagram of another embodiment of the valve housing having a lumen selector according to the present invention.

As shown in FIGS. 2 and 3, a valve assembly 202 according to an exemplary embodiment of the present invention includes a lumen selector selectively connecting to the catheter lumen either the power injection flow path or the infusion port flow path to prevent back flow from the power injection flow path into the infusion port flow path. This selector may be operated manually by a user of the catheter or may automatically move to a configuration corresponding to the connection of a device to one or the other of the power injection and infusion ports. That is, the valve assembly 202 may include a mechanism which, whenever a device is coupled to the power injection port, moves the selector to a position permitting flow from the power injector to the catheter and preventing back flow to the infusion port.

As shown in FIGS. 2 and 3, the valve and connector component 200 comprises an infusion access site 210 with a flow passage 214 in fluid connection with the lumen 218 of the catheter 104 and a power injection access site 212 opening to a flow passage 216 also in fluid connection with the lumen 218. A PASV 220 is located in the flow passage 214, upstream from the junction with the flow passage 216. The valve housing 202 thus comprises two flow passages that merge into one lumen of the catheter 104. The two separate flow passages have corresponding access sites 210, 212 adapted for connection with external medical devices that provide low pressure or high pressure fluids, as needed.

As described above, a lumen selector 250 of the valve assembly 202 prevents high pressure fluids introduced through the power injection access site 212 from applying excessive back pressure to the distal face 223 of the slitted membrane 222. For example, the lumen selector 250 may comprise a partition 252 movable about a pivot point 254 through an angle α between positions A and B of FIG. 2. In position A, the partition 252 closes off from the lumen of the catheter 104 the flow passage 216 of the power injection access site 212 and, in position B, the partition 252 closes off from the lumen of the catheter 104 the infusion access site 210 and the associated flow passage 214. Thus, when performing a power injection, the partition 252 is placed in position B, preventing fluid from backing up against the distal side of the slitted membrane 222.

As shown in FIG. 3, the valve body 202 according to this embodiment comprises an external selector 300 that rotates on a pivot 302 to operate the partition 252. The selector 300 may be hand operated by the user to selectively close the power injection lumen 216 or the infusion lumen 214, as desired. Markings may be provided on the valve housing 202 to illustrate the orientation of the partition 252 relative to the position of the external selector 300 as would be understood by those skilled in the art. In the exemplary embodiment, the external selector 300 rotates on a pivot 302 that is the same or is mechanically linked to the pivot 254 of the partition 252. However, different methods of moving the partition 252 may be used, such as for example mechanical linkages, spring loaded mechanisms, pressure actuated mechanisms and powered components.

Those skilled in the art will understand that, instead of the lumen selector, a check valve may be installed in the infusion passage permitting flow distally therethrough while preventing backflow at all times. The power injection port may then be sealed by a simple cap.

The present invention has been described with reference to specific embodiments, and more specifically to a connector used alternatively for power injecting a fluid and to infuse a fluid into a valved PICC. However, other embodiments may be devised that are applicable to other medical devices, without departing from the scope of the invention. Accordingly, various modifications and changes may be made to the embodiments, without departing from the broadest spirit and scope of the present invention as set forth in the claims that follow. The specification and drawings are accordingly to be regarded in an illustrative rather than restrictive sense.

What is claimed is:

1. A valve assembly for a catheter comprising:
    a housing having a lumen extending at least partially therethrough, the lumen having a proximal end and a distal end;
    a first port opening in fluid communication with the proximal end of the lumen via a first port passage, the first port passage having a first longitudinal axis;
    a valve disposed in the first port passage, the valve being biased toward a closed configuration to prevent fluid flow therethrough when the first port passage is not in use;
    a second port opening in fluid communication with the proximal end of the lumen via a second port passage, the second port passage having a second longitudinal axis;
    a passage selector located distally of the valve; and
    an external actuator for manual operation of the passage selector, the external actuator configured to switch the passage selector between a first and second position;
    wherein the first and second port passages merge distally of a vertical plane containing the valve,
    wherein the first position prevents fluid communication between the distal end of the lumen and the valve,
    wherein the second position prevents fluid communication between the distal end of the lumen and the second port, and
    wherein the first longitudinal axis assumes an acute angle with the second longitudinal axis proximal of the merge.

2. The valve assembly according to claim 1, wherein the valve is a pressure actuated safety valve (PASV).

3. The valve assembly according to claim 2, wherein the PASV comprises a slitted membrane extending across the first port passage.

4. The valve assembly according to claim 1, wherein the passage selector automatically closes the first port passage during use of the second port passage.

5. The valve assembly according to claim 1, further comprising a connector for coupling to a catheter.

6. The valve assembly according to claim 1, wherein the valve assembly is permanently coupled to a catheter.

7. A method of using a catheter comprising:
providing a catheter having a valve assembly,
the valve assembly comprising:
a housing having a lumen extending at least partially therethrough, the lumen having a proximal end and a distal end,
a first port opening in Mild communication with the proximal end of the lumen via a first port passage, the first port passage having a first longitudinal axis,
a valve disposed in the first port passage, the valve being biased toward a closed configuration to prevent fluid flow therethrough when the first port passage is not in use,
a second port opening in fluid communication with the proximal end of the lumen via a second port passage, the second port passage having a second longitudinal axis,
a passage selector located distally of the valve, configured to switch between a first and second position,
wherein the first and second port passages merge distally of a vertical plane containing the valve,
wherein the first position prevents fluid communication between the distal end of the lumen and the valve,
wherein the second position prevents fluid communication between the distal end of the lumen and the second port, and
wherein the first longitudinal axis assumes an acute angle with the second longitudinal axis proximal of the merge:
the catheter comprising:
a conduit in fluid communication with the distal end of the lumen;
inserting a distal end of the catheter to a target site within a human body;
manually moving the external actuator to select the first position;
connecting a power injection system to the second port;
power injecting a fluid through the second port and to the target site via the conduit.

* * * * *